United States Patent [19]

Uffenheimer

[11] Patent Number: 5,558,838
[45] Date of Patent: Sep. 24, 1996

[54] SAMPLE PREPARATION APPARATUS

[75] Inventor: Kenneth F. Uffenheimer, Los Gatos, Calif.

[73] Assignee: Becton Dickinson and Company, Franklin Lakes, N.J.

[21] Appl. No.: 129,634

[22] Filed: Sep. 29, 1993

[51] Int. Cl.⁶ ........................................................ B01L 3/02
[52] U.S. Cl. .................. 422/100; 73/864.12; 73/864.15; 73/864.22; 73/864.24; 422/63; 422/81
[58] Field of Search ................................ 422/100, 81, 63; 436/49, 54; 73/864.11, 864.12, 864.15, 864.22, 864.24

[56] References Cited

U.S. PATENT DOCUMENTS

| D. 277,891 | 3/1985 | Uffenheimer et al. |
|---|---|---|
| 3,719,086 | 3/1973 | Bannister et al. |
| 3,872,730 | 3/1975 | Ringrose et al. |
| 3,885,438 | 5/1975 | Harris, Sr. et al. |
| 3,954,341 | 5/1976 | Uffenheimer. |
| 4,000,973 | 1/1977 | Petersen. |
| 4,244,919 | 1/1981 | Chen. |
| 4,282,182 | 8/1981 | Webster .................................. 422/100 |
| 4,311,484 | 1/1982 | Fosslien. |
| 4,313,735 | 2/1982 | Yamashita et al. |
| 4,318,885 | 3/1982 | Suzuki et al. .......................... 73/864.22 |
| 4,357,301 | 11/1982 | Cassaday et al. |
| 4,475,411 | 10/1984 | Wellerfors. |
| 4,517,850 | 5/1985 | Wiseman et al. |
| 4,602,995 | 7/1986 | Cassaday et al. |
| 4,629,703 | 12/1986 | Uffenheimer. |
| 4,673,404 | 6/1987 | Gustavsson. |
| 4,683,212 | 7/1987 | Uffenheimer. |
| 4,756,201 | 7/1988 | Uffenheimer. |
| 4,758,409 | 7/1988 | Uffenheimer. |
| 4,774,057 | 9/1988 | Uffenheimer et al. |
| 4,799,393 | 1/1989 | Uffenheimer. |
| 4,808,381 | 2/1989 | McGregor et al. |
| 4,811,611 | 3/1989 | Uffenheimer. |

(List continued on next page.)

FOREIGN PATENT DOCUMENTS

WO84/04672  12/1984  WIPO.
WO84/04673  12/1984  WIPO.

OTHER PUBLICATIONS

Baxter Healthcare Corp., Paramax® Enhancements, Jul. 1990 IQ "New Software MC 2.0".
"Serumax® II", Medical Robotics, Inc.

Primary Examiner—Jeffrey R. Snay
Assistant Examiner—Jan M. Ludlow
Attorney, Agent, or Firm—Allen W. Wark

[57] ABSTRACT

A sample preparation apparatus includes a pair of valves. A first valve selectively communicates a sample tube with a vent/aspiration valve, or alternatively communicates a diluent pump with a reaction tube. By moving the first valve, one may selectively relieve a vacuum within a sample tube, aspirate a sample from the tube, or alternatively may drive a diluent and a sample into the reaction tube. The second valve is a vent/aspiration valve which selectively communicates the first valve to two distinct systems. A first system vents a vacuum in the sample tube, and a second system aspirates a sample from the sample tube. The second valve is actuated to initially relieve any vacuum in the sample tube, and is then actuated to connect the aspiration system to the sample tube to begin to withdraw of a sample from the sample tube. At the same time, the diluent pump is filled. The shear valve is then moved to communicate the diluent pump to the reaction tube. The diluent pump is actuated to drive a diluent and a sample slug into the reaction tube, which preferably contains a predispensed reagent. This system simplifies the valving structure over the prior art systems. In addition, a unique rinse system provides a rinse solution to the outer periphery of the needle, while the needle is connected to a source of suction to withdraw the rinse fluid. Finally, a unique structure for holding and properly positioning the reaction tube provides a control signal indicating that a reaction tube is received in the reaction tube structure. If no reaction tube is sensed, a controller deactivates the system such that no fluids are dispensed by the system.

12 Claims, 8 Drawing Sheets

U.S. PATENT DOCUMENTS

| | | | |
|---|---|---|---|
| 4,817,443 | 4/1989 | Champseix et al. | 73/864.22 |
| 4,836,038 | 6/1989 | Baldwyn . | |
| 4,863,066 | 9/1989 | Uffenheimer . | |
| 4,928,539 | 5/1990 | Champseix et al. . | |
| 4,951,512 | 8/1990 | Mazza et al. | 422/64 |
| 4,984,475 | 1/1991 | Uffenheimer et al. . | |
| 4,997,768 | 3/1991 | Uffenheimer et al. . | |
| 5,012,845 | 5/1991 | Averette . | |
| 5,101,673 | 4/1992 | Uffenheimer et al. . | |
| 5,133,218 | 7/1992 | Uffenheimer et al. . | |
| 5,201,232 | 4/1993 | Uffenheimer . | |
| 5,215,714 | 6/1993 | Okada et al. . | |
| 5,216,926 | 6/1993 | Lipscomb | 73/864.22 |
| 5,229,074 | 7/1993 | Heath et al. . | |

SAMPLE PREPARATION APPARATUS

BACKGROUND OF THE INVENTION

This application in general relates to an apparatus for preparation of a blood sample which dispenses measured amounts of a blood sample and a diluent into a reaction tube which contains a predispensed reagent.

Sample preparation systems are known in the prior art, and may include needles which pierce a closure on a sample tube to provide communication between blood in the sample tube and the system.

In general, complicated valving systems have been utilized to withdraw an amount of a blood sample from a closed blood sample tube, and move that blood sample to a reaction tube. Many prior art systems use a diluent as a means of assisting the movement of the blood sample through the system. In the complicated prior art systems, the amount of diluent required has been undesirably large. Thus, the blood reaching the reaction tube is overly diluted and reactions within the reaction tube require an undesirably long period of time.

It is known in the prior art to aspirate blood from the sample tube through the needle, and to a reaction tube by connecting the needle to a source of suction such as a pump. In one such prior art system disclosed in the U.S. Pat. No. 4,811,611, the aspiration system which is used to withdraw blood from the tube through the needle initially contains a charge of air. As the needle punctures the closure in the tube, this charge of air communicates with the tube, relieving a vacuum in the tube. A problem with the use of such prior art systems is that a fixed charge of air is typically utilized. In so-called "short draw" sample tubes wherein there is an unusually small amount of blood, there may be a greater vacuum in the sample tube. In such cases, the charge of air in the prior art system may be insufficient to fully relieve the vacuum. Further, the use of the aspiration system to relieve vacuum in the tube results in a complex aspiration system including a number of valves. It would be desirable to reduce the complexity of the aspiration system.

In addition, in the prior art system disclosed in the above referenced patent the valving between the sample tube, the reaction tube, and the diluent pump is somewhat complicated. It would be desirable to reduce the complexity of the valving for the various systems.

Also, the known systems for rinsing or cleaning the needle after removing a sample from the sample tube is somewhat complicated and inefficient.

Finally, the prior art systems have typically used fixed reaction chambers.

SUMMARY OF THE INVENTION

In a disclosed embodiment of a sample preparation apparatus according to this invention, a pair of valves including a first shear valve and a second vent/aspiration valve control the flow between a sample tube, a reaction tube, the atmosphere, a waste pump, and a diluent pump. The inventive valving reduces the complexity of the system, and quickly and efficiently connects the various operational members to provide the appropriate flow of fluids between the members. The shear valve selectively connects a line leading to the vent/aspiration valve to the sample tube, or alternatively connects the diluent pump to a line leading to the reaction tube. In one main feature of this invention, the vent/aspiration tube alternatively connects one of a source of atmosphere and a connection to a pump, through the shear valve and to the sample tube. When the needle initially pierces the sample tube, the vent/aspiration valve is connected to the source of atmospheric air, relieving any vacuum in the tube. The amount of blood in the sample tube has no effect of the ability of the inventive system to relieve the vacuum. Since the tube is connected to a source of atmosphere, rather than a pre-set limited charge of air, the vacuum is fully relieved. In addition, since the sample is connected to the atmosphere, no complicated valving system is required as is necessary in the prior art.

The diluent pump is preferably operated at a relatively high velocity such that the diluent fluid leading to the various passages and moving the sample into the reaction tube moves at a similarly high velocity. This reduces the amount of diluent necessary to move the required blood sample, while still ensuring low sample carryover. This thus reduces the amount of dilution to the blood sample, and decreases the required reaction time once the blood is in the reaction tube.

In another disclosed feature of the present invention, a rinse line is connected to a chamber surrounding the outer peripheral surface of the needle. After aspiration of a sample from a tube, the needle is retracted into the chamber, rinse fluid is communicated into the chamber, and rinses the needle and the sample flow path. A waste pump is connected to the needle and withdraws the rinse fluid from the chamber and through the sample flow path.

In another disclosed feature of this invention, a tube for holding the reaction tube includes structures which are biased between a "no tube" position and a "tube holding" position. A sensor determines whether a portion of the tube holder is in a location which identifies receipt of a tube. In the absence of a tube, an over-ride signal is sent to a controller preventing dispensing of any fluid from the system without the presence of a reaction tube.

The reaction tube holding structure preferably includes a pair of pivoting members which are spring biased to a "no tube" position. In this position a contact preferably contacts the sensor, such that the sensor can determine that there is no tube in the reaction tube holding structure. At the same time a second portion of the reaction holding structure is pivoted to a position where it will easily accept the reaction tube, as the reaction tube is moved into the holding structure. Preferably, this second portion is an upper holding portion which includes a magnet which holds the upper portion at the "tube holding" position. At the same time, the lower tube holding member is forced away from a no tube position by receipt of the tube. A reaction bias force securely holds the reaction tube in place and also ensures that it is properly positioned relative to a dispensing nozzle. This is important to ensure that the blood, diluent and reagent are substantially mixed.

These and other features of the present invention can be best understood from the following specifications and drawings, of which the following is a brief description.

DETAILED DESCRIPTION OF THE PREFERRED EMBODIMENT

Figure 1:
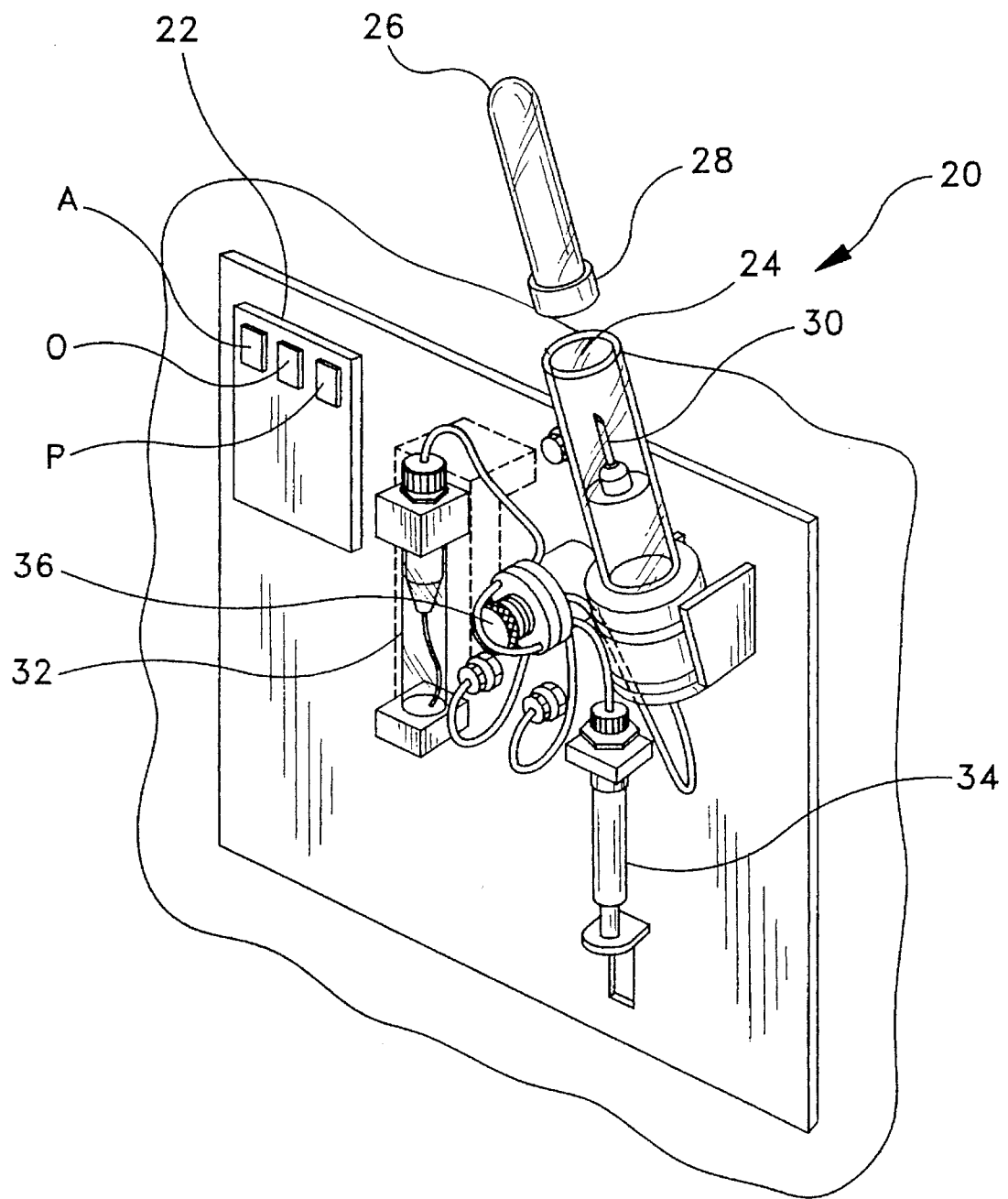
FIG. 1 is a perspective view of a sample preparation apparatus according to the present invention.

A sample preparation apparatus 20 is illustrated in FIG. 1 including a control panel 22 for controlling the operation of the system. A tube guide 24 receives a closed sample tube 26 including closure 28. Tube guide 24 guides sample tube 26 downwardly onto a needle 30 which punctures the closure 28. As will be explained below, any vacuum in the tube will be vented at that time. The sample may then be aspirated from the sample tube 26 and delivered to a reaction tube 32. A diluent pump 34 communicates to the reaction tube 32 through a shear valve 36. Preferably, reaction tube 32 contains a predispensed reagent.

Figure 2:
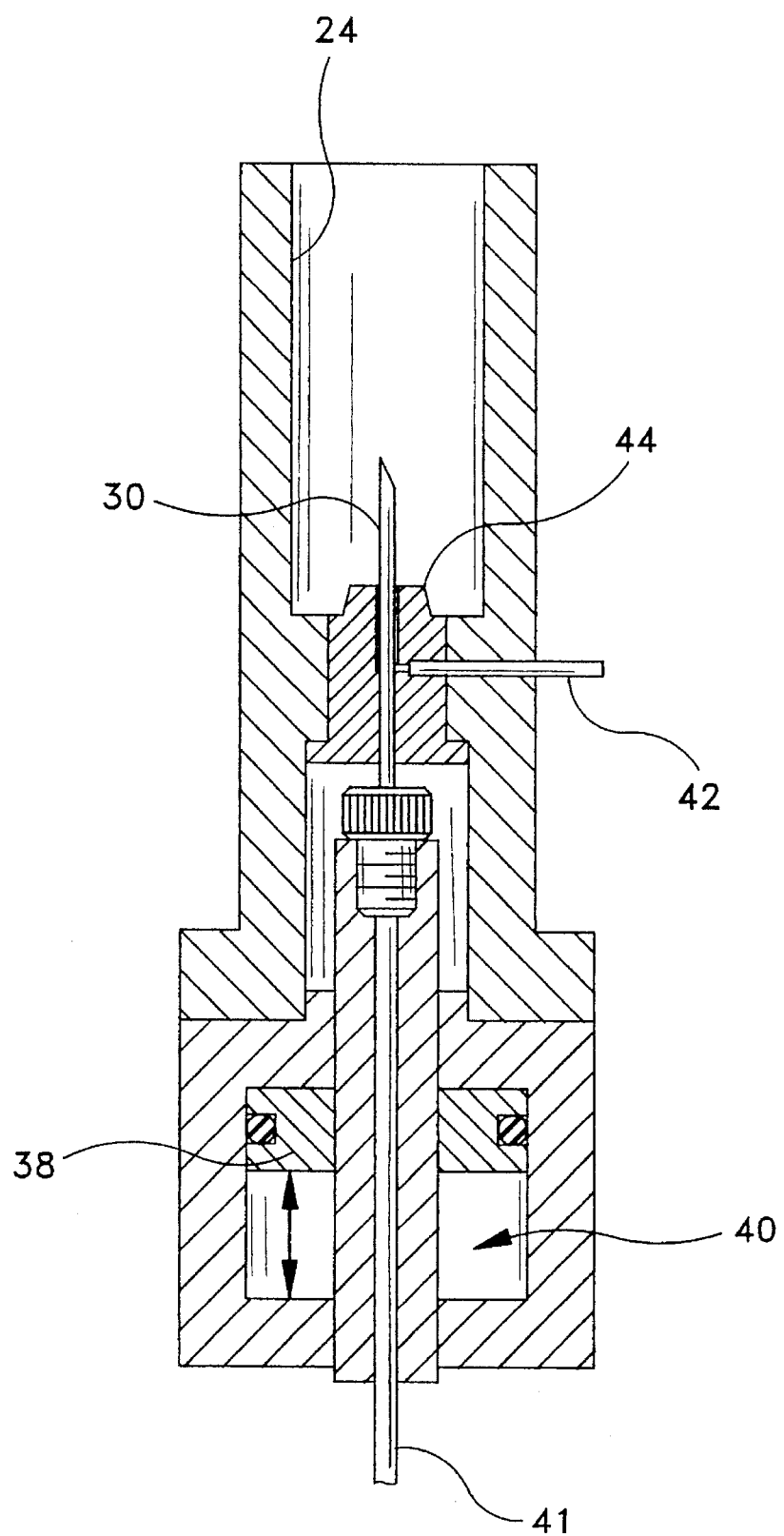
FIG. 2A is a schematic view of the main operational members of the apparatus illustrated in FIG. 1.
FIG. 2B shows additional features of a portion of the apparatus shown in FIG. 2A.
Figure 2A:
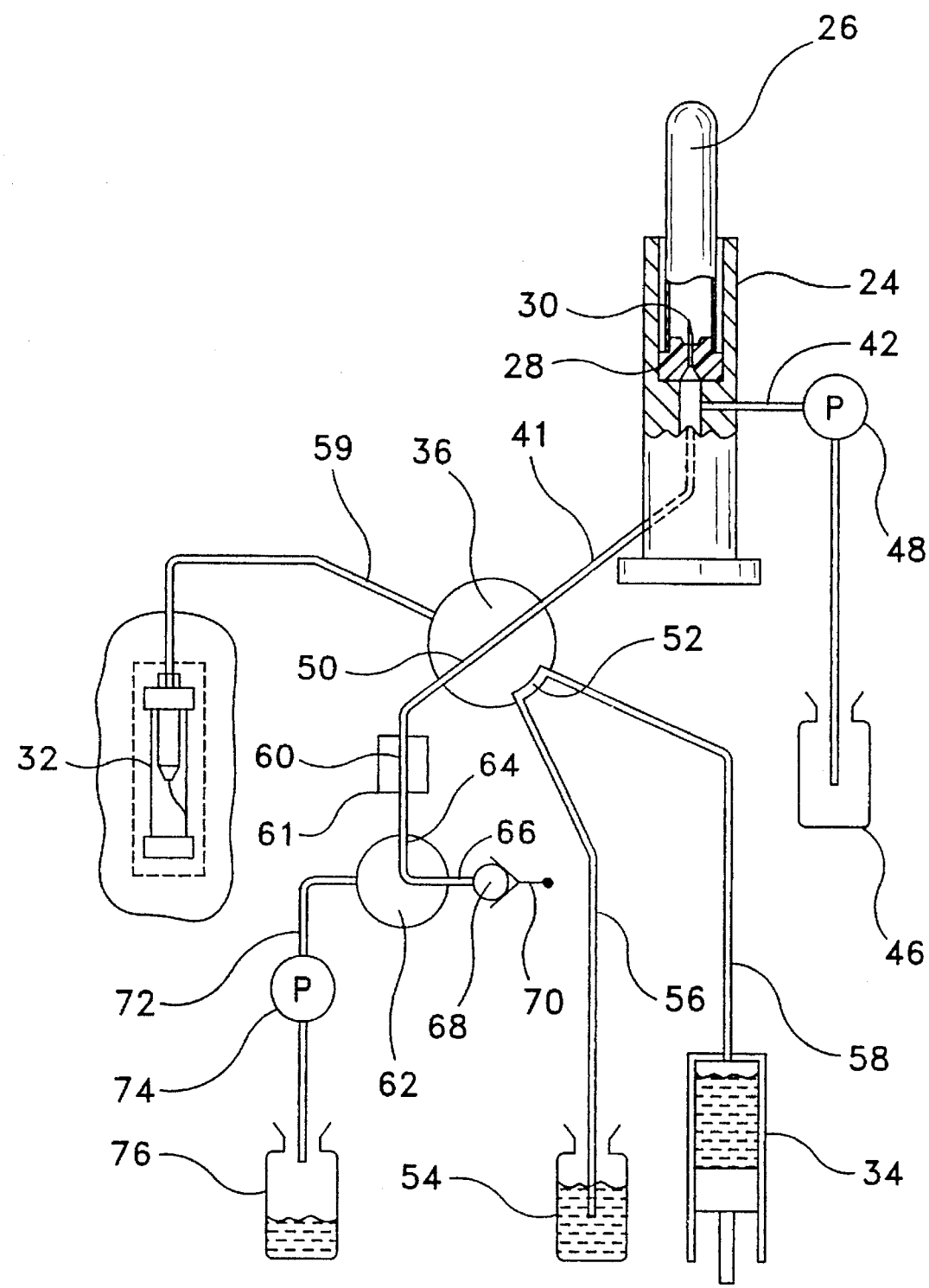

As shown in FIG. 2A, needle 30 has punctured the closure 28 and line 41 communicates with the interior of sample tube 26 through needle 30. As shown in FIGS. 2A, and 2B, a rinse line 42 communicates with a chamber 44 at the outer periphery of the needle 30. Rinse line 42 is connected to a rinse fluid 46 through a pump 48. As will be explained below, after a sample is aspirated from sample tube 26, needle 30 is retracted and rinse fluid is delivered to chamber 44 to clean needle 30.

As also shown, a sample loop or passage 50 extends through shear valve 36. In addition, a groove 52 connects a diluent fluid 54 through a line 56 to a line 58 leading to diluent pump 34.

As shown in FIG. 2A, shear valve 36 is in a position where passage 50 communicates line 41 from needle 30 to a passage 60. Passage 60 will be termed a "valve passage" for purposes of this application as it connects the two main valves of this invention. Passage 60 passes through conductivity detector 61, and communicates with a vent/aspiration valve 62 having a passage 64. In the position shown in FIG. 2A, passage 64 communicates passage 60 to a passage 66 leading to a check valve 68 which is in turn connected to atmosphere at 70. A conduit or line 72 is selectively communicated with passage 64 to communicate a pump 74 and waste reservoir 76 to line 60. In a second position of shear valve 36, a passage 59 is communicated through shear valve 36 to the diluent pump 34 to send a sample and diluent to the reaction tube 32, as will be explained below.

As shown most clearly in FIG. 2B, a piston 38 is connected to needle 30, and an air cylinder 40 facilitates movement of the piston 38 and in turn reciprocation of needle 30, as will explained in greater detail below. In one disclosed embodiment of this invention, an air compressor (not shown) is connected to drive piston 38, and also to drive a piston for diluent pump 34. As shown, line 41 extends coaxially to needle 30 such that line 41 will not be twisted by any movement of piston 38.

When it is desired to aspirate a sample from sample tube 26, the shear valve 36 and vent/aspiration valve 62 are moved to the positions shown in FIG. 2A. The tube 26 is moved downwardly such that needle 30 punctures closure 28. At that time, atmosphere communicates through passage 70, check valve 68, passages 66, 64, 60, 50, 41 and through needle 30 into the interior of sample tube 26. Thus, should a vacuum exist in sample tube 26, that vacuum will be relieved. Since the vacuum is connected to atmosphere it will be fully relieved by being equalized with the atmosphere, regardless of how much blood is in tube 26.

Figure 3:
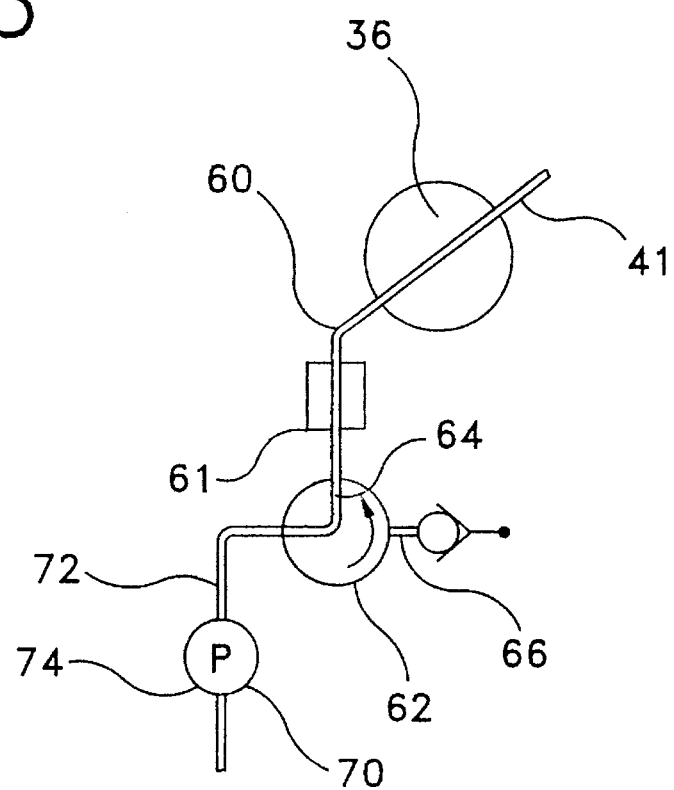
FIG. 3 shows a subsequent position for the valves shown in FIG. 2A.

The aspiration system for aspirating a portion of the sample from the tube 26 is then actuated, and the vent system for communicating atmosphere to the tube is disconnected by turning vent/aspiration valve 62 to the position shown in FIG. 3 such that valve passage 64 connects valve passage 60 to passage 72. Pump 74 is started, and conductivity detector 61 is armed. A sample of the blood within tube 26 is then aspirated through needle 30, passage 41, passage 50, and into valve passage 60. Once the conductivity detector 61 identifies the beginning of the slug of sample, pump 74 is deactuated.

The vent/aspiration valve 62 is then returned to the position shown in FIG. 2A. The needle 30 is retracted by actuating the cylinder 40 and reciprocating piston 38 downwardly from the position shown in FIG. 2B. Prior to this time, the diluent pump 34 has been retracted, and a measured amount of diluent has been aspirated from source 54 through passages 56, 52 and 58, and into diluent pump 34.

Figure 4:
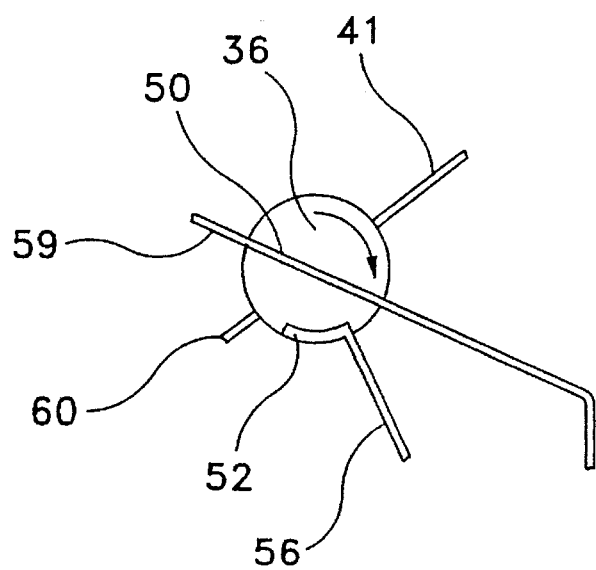
FIG. 4 shows yet another subsequent position for one of the valve shown in FIG. 2A.

Shear valve 36 is then rotated from the position shown in FIG. 2A to the position shown in FIG. 4. As shear valve 36 rotates, a predetermined amount of the sample is trapped in passage 50, such that sample is now between passages 58 and 59.

Diluent pump 34 is then actuated, and flushes the trapped sample volume in passage 50 along with the diluent into reaction tube 32, which preferably contains a pre-dispensed reagent. The cross-sectional area of passages 58 and 59, and the velocity of the diluent pump 34 are selected such that the velocity of the diluent will be rather high. In this way, the amount of diluent required to move the sample from passage 50, and through passage 59 into reaction tube 32 is smaller than is required in the prior art. In addition, the diluent will efficiently remove the sample from passage 50 and passage 59, leaving little if any residual sample in passage 59 after the sample is dispensed into reaction tube 32.

After the sample and diluent are dispensed into reaction tube 32, shear valve 36 is rotated from the position shown in FIG. 4 back to the position shown in FIG. 2A and the vent/aspiration valve 62 is returned to the position shown in FIG. 3. Waste pump 74 and rinse pump 48 are actuated. Rinse solution flows from bottle 46 through passage 42 into the annular chamber 44 surrounding the retracted needle 30. As the rinse solution moves into the area surrounding the needle 30, waste pump 74 draws the solution through needle 30, passages 41, 50, 60, 64, 72 and into waste reservoir 76. Rinse pump 48 is then deactuated and pump 74 continues to run, air-drying the entire flow path of needle 30, and passages 41, 50, 60, 64 and 72. Also, the diluent pump piston is withdrawn to recharge the pump.

Needle 30 is again extended into the up position, waste pump 74 is deactuated and vent/aspiration valve 62 is returned to the position shown in FIG. 2A. The reaction tube is replaced and the system is then ready to take another sample.

Figure 5:
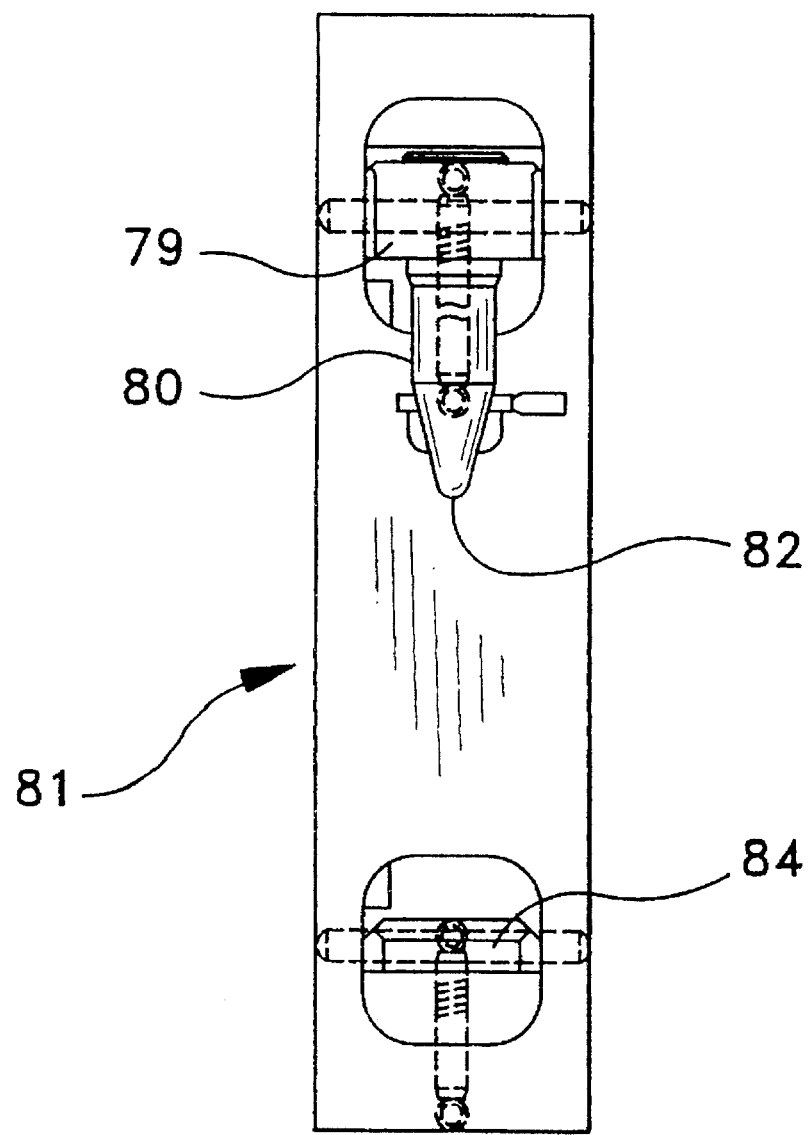
FIG. 5 is a view of a portion of the structure illustrated in FIG. 2A.

As shown in FIG. 5, the holding structure 81 for the sample tube 32 includes a nozzle 80 having a dispensing end 82 connecting to a top holding structure 79. A lower holding structure 84 is spaced from upper holding structure 79.

Figure 6:
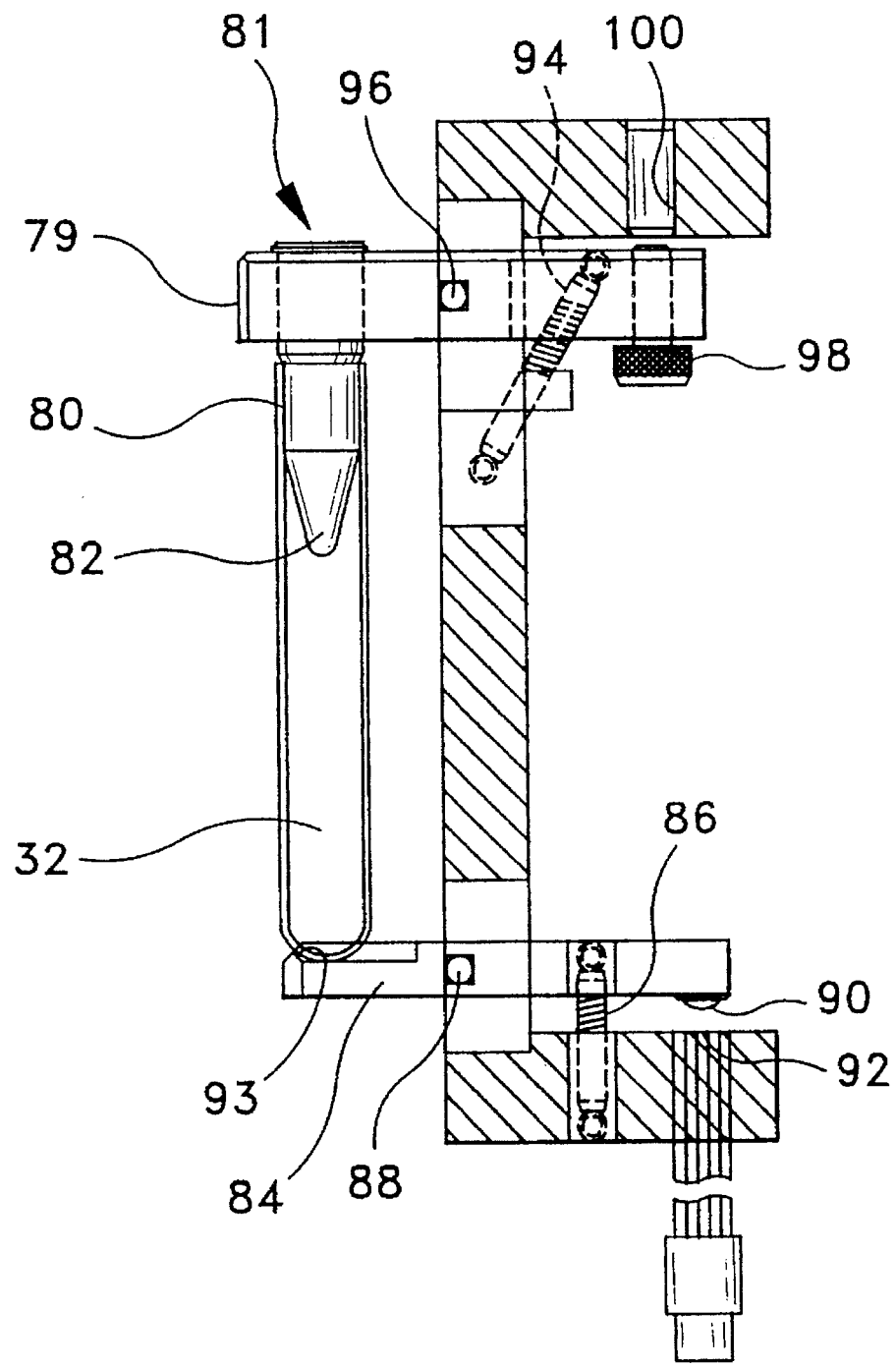
FIG. 6 is a side view of the portion shown in FIG. 5, in a tube holding position.

As shown in FIG. 6, lower holding structure 84 includes a spring 86 pivoting lower holding structure 84 about pivot point 88. A point 90 at an inner end of lower holding structure 84 is spaced from sensor 92. Sensor 92 determines whether a tube 32 is received on holding structure 81. In the "tube holding" position of FIG. 6, there is no contact between sensor 92 and point 90. If no tube is sensed, the sensor 92 operates through the controller to deactivate the system and prevent any solution from being dispensed through dispensing end 82. A wedge 93 on lower holding structure 84 holds tube 32 at a desired position and orientation to ensure adequate mixing of sample, reagent and diluent.

A spring 94 causes upper end 79 to pivot about pivot point 96. A member 98 secures upper member 79 in the holding position by being attracted to magnet 100. Preferably a rare earth magnet is used which easily overcome the force of spring 94.

Figure 7:
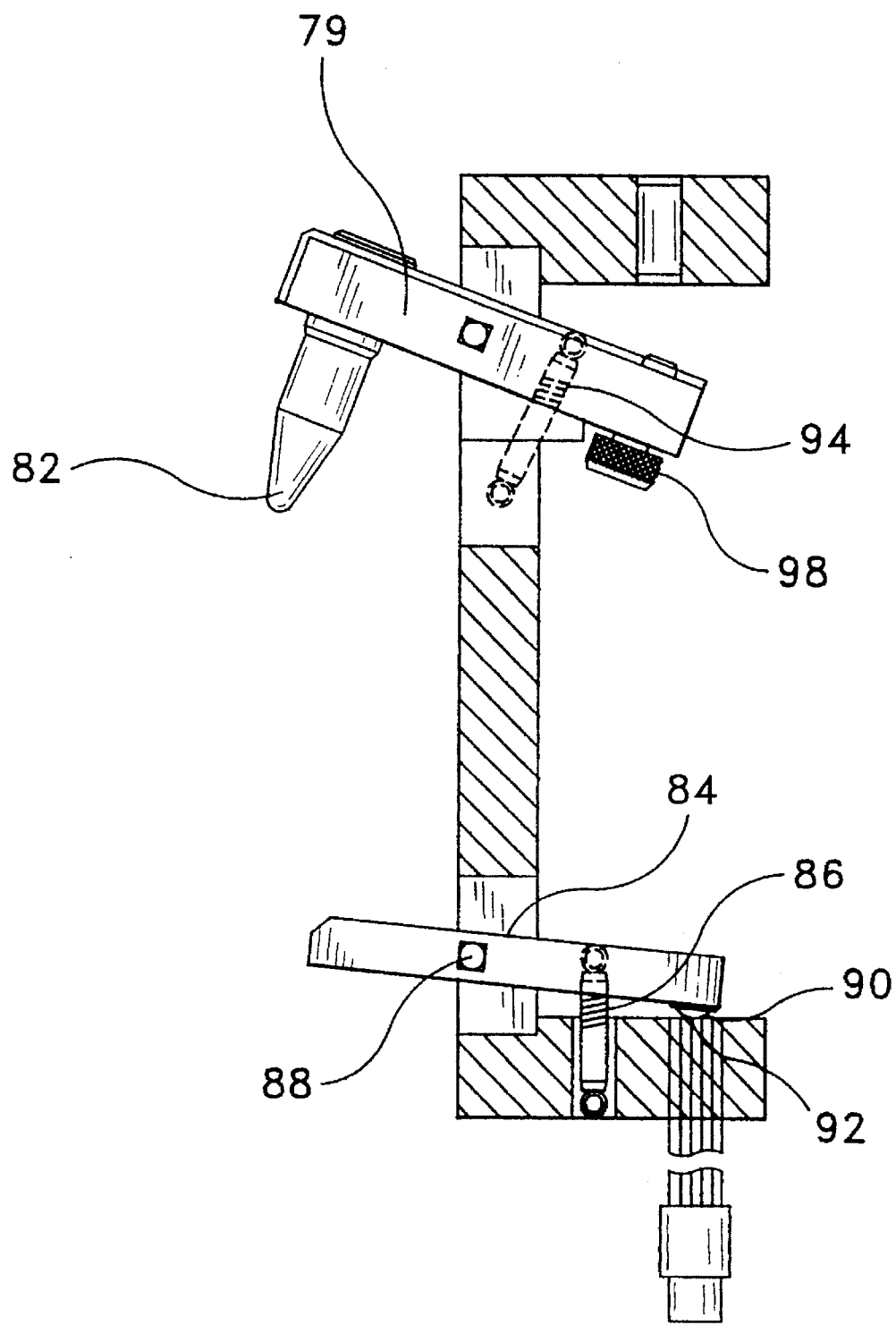
FIG. 7 illustrates the structure of FIG. 6 in "no tube" position.

As shown in FIG. 7, with no tube being held, springs 86 and 94 pivot lower holding member 84 and upper holding member 79, respectively, to upwardly pivoted positions. With lower holding member in this "no tube" position, point 90 contacts sensor 92. Sensor 92 may then determine that there is no reaction tube 32 received in the holding structure 81, and the appropriate control signals are initiated.

As shown in FIG. 7, nozzle 80 has dispensing end 82 which is conically shaped and positioned facing downwardly and away from the remainder of the reaction tube holding structure. In this way, a reaction tube may be easily inserted onto dispensing end 82, and the upper holding structure 79 may then be moved towards a position where member 98 is attracted to magnet 100. The upper portion is held at the location such as shown in FIG. 6. At the same time the lower holding structure 84 may be forced downwardly such that it underlies the reaction tube. The lower holding structure 84 would then be released, and it would be biased towards the position shown in FIG. 6. This bias force secures the reaction tube 32 to the reaction tube holding structures 81. In addition, wedge 93 ensures the tube is held in a proper orientation.

Figure 8:
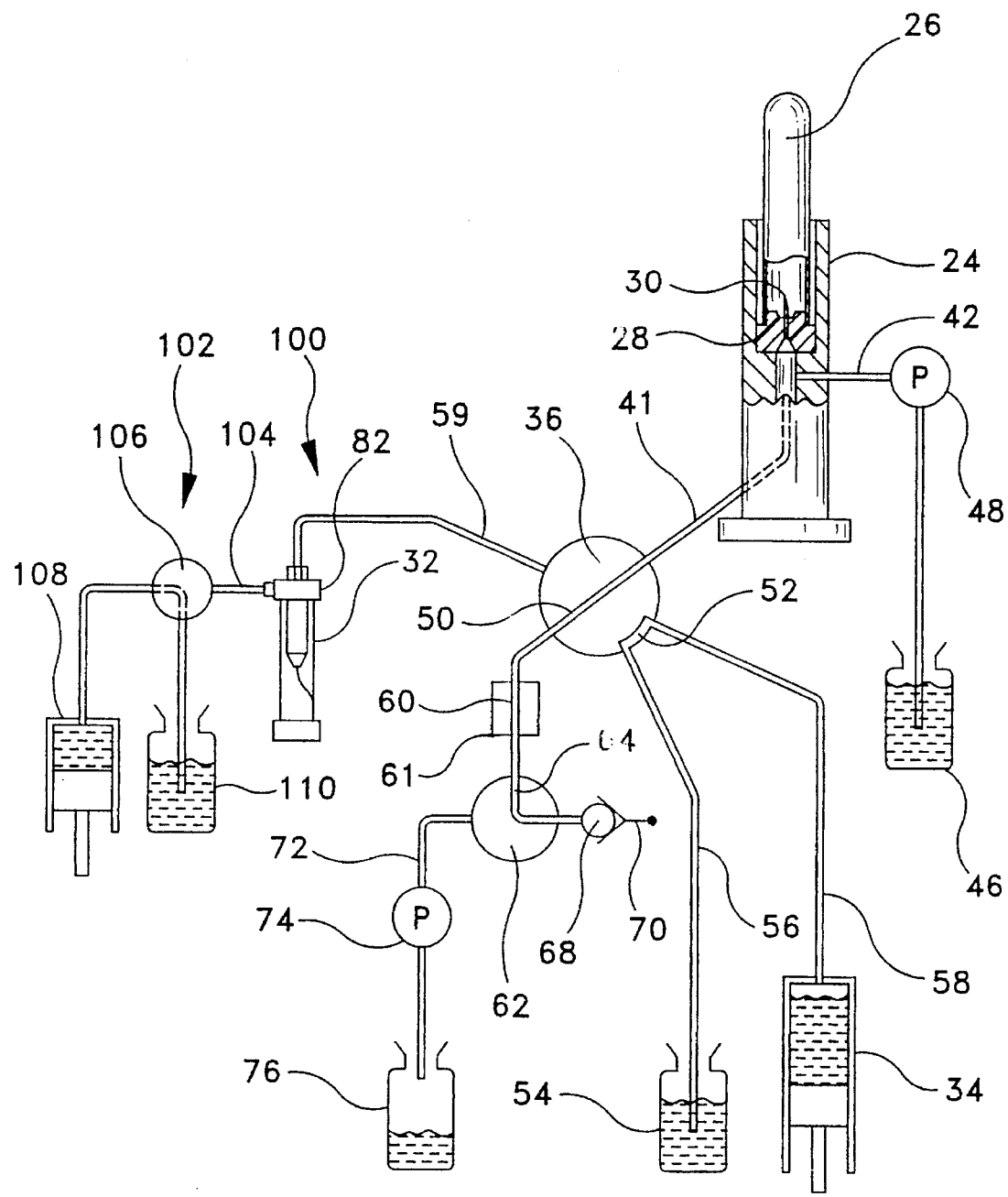
FIG. 8 is a view similar to FIG. 2A but showing an alternative system.

A second embodiment 100 is illustrated in FIG. 8. Second embodiment 100 is identical to the system shown in FIG. 2A, except, a reagent supply branch 102 is connected to dispensing end 82 associated with reaction tube 32. A passage 104 extends from dispensing end 82 to valve 106. Valve 106, shown schematically, alternatively connects a pump 108 to dispensing end 82, or alternatively connects pump 108 to a supply of reagent 110. A measured quantity of a second reagent is aspirated into pump 108 from container 110 through valve 106. Valve 106 is then moved to directly connect pump 108 to dispensing end 82. The reagent is then dispensed into dispensing end 82 by actuating pump 108. The second reagent may be a lysing agent.

As a further alternative to either of the systems shown in FIG. 2A or FIG. 8, the diluent driven by pump 34 may be a reagent, rather than a diluent.

As a further feature, needle 30 may have a titanium nitride coating to provide a hard wear resistant surface.

In various control features according to the present invention, the controller panel 22 includes an aspirate button A which initiates aspiration of the blood from the sample tube according to the method disclosed above. Further, there is a manual override button O which may be utilized to dispense a diluent or reagent into the reaction tube in situations where the blood sample has been manually pipetted into the reaction tube 32. Further, a power button P is actuated to initiate a system self check and a reset after a power off condition. A power off condition retracts the needle.

The controller preferably senses and acts upon the following error conditions: waste container over-pressure which indicates an unduly large amount of waste in container 76; a sample not aspirated in a particular amount of time condition, which may indicated either a system failure, or an improper sample; a shear valve rotation error which monitors the desired position of the shear valve at the particular point in the operation of the system; a diluent pump error; and finally, a reaction tube not in place error signal. Appropriate sensors are included to effect these error signals.

A preferred embodiment of this invention has been disclosed, however, a worker of ordinary skill in the art would recognize that certain modifications would come within the scope of this invention. For that reason, the following claims should be studied to determine the true scope and content of this invention.

What is claimed is:

1. A sample preparation system comprising:

a sample tube holding structure, and a flow passage leading from said sample tube holding structure;

a reaction tube holding structure, and a reaction tube passage leading into said reaction tube holding structure;

a diluent pump in communication with a source of a diluent for moving said diluent along a diluent passage upon actuation of said diluent pump;

a vent passage leading to atmosphere;

a suction passage leading to a source of suction;

a first valve alternatively communicating said flow passage to a valve passage, or communicating said diluent passage to said reaction tube passage; and a second valve selectively communicating said valve passage to said suction passage or said vent passage.

2. A sample preparation system as recited in claim 1, wherein said vent passage is in communication with atmosphere through a check valve, which prevents aerosols from being liberated to the atmosphere.

3. A sample preparation system as recited in claim 2, wherein said sample holding structure includes a needle which is selectively communicable with said vent passage when the first and second valves are in appropriate positions, such that atmosphere is communicated through said needle to relieve any vacuum in a sample tube received on said sample tube holding structure.

4. A sample preparation system as recited in claim 3, wherein said source of suction includes a waste pump connected to a waste reservoir.

5. A sample preparation system as recited in claim 1, wherein said sample tube holding structure includes a needle such that said needle can puncture a closure in a sample tube, and communicate a sample in the sample tube to said sample tube passage, and said sample tube holding structure is connected to a rinse passage for selectively communicating a rinse fluid to an outer surface of said needle to clean said needle, and said suction passage being selectively communicated to said needle through said first and second valves as said rinse fluid is being dispensed, such that said rinse fluid is removed through said needle and into said suction passage to clean said suction passage and remove said rinse fluid.

6. A sample preparation system as recited in claim 5, wherein said sample tube holding structure includes a rinse chamber surrounding an outer peripheral surface of said needle so that said rinse fluid is dispensed into said rinse chamber.

7. A sample preparation system as recited in claim 6, wherein said needle is retractable relative to said sample holding structure.

8. A sample preparation system assembly as recited in claim 1, wherein said first valve includes a first passage for selectively communicating said reaction tube passage to said diluent passage and said flow passage to said valve passage, and said first valve also includes a second passage which communicates said diluent source with said diluent pump when said first passage of said first valve connects said flow passage with said valve passage.

9. A sample preparation apparatus as recited in claim 1, wherein said reaction tube holding structure includes a sensor which determines whether a reaction tube is received in said reaction tube holding structure, said sensor being incorporated into a control for the sample preparation system such that no fluids are communicated to said reaction tube passage if no reaction tube is sensed.

10. A sample preparation system as recited in claim 9, wherein said reaction tube holding structure includes a lower pivoting member pivoting between two positions, and having a first portion spaced from said sensor when said reaction tube is received in said reaction tube holding structure, and said first portion contacting said sensor when no reaction tube is sensed.

11. A sample preparation system as recited in claim 10, wherein an upper pivoting member is positioned adjacent to an upper end of said reaction tube, and said lower pivoting member receives a lower end of said reaction tube, said upper pivoting member also pivoting between two positions, with both said lower and upper pivoting members being biased to pivot towards a first position in the absence of a reaction tube.

12. A sample preparation system as recited in claim 11, wherein said upper pivoting member includes a nozzle for dispensing said sample and diluent into an open end of said reaction tube, said upper pivoting member being biased to accommodate receipt of said reaction tube over said nozzle.

* * * * *